US010500335B2

(12) United States Patent
Koppelman et al.

(10) Patent No.: US 10,500,335 B2
(45) Date of Patent: Dec. 10, 2019

(54) MEDICAMENT DELIVERY DEVICE SUB-ASSEMBLY

(71) Applicant: CONSORT MEDICAL PLC, Hemel Hempstead (GB)

(72) Inventors: Rachel Koppelman, Cambridge (GB); Alan Judd, St. Neots (GB); Alastair Willoughby, Cambridge (GB)

(73) Assignee: CONSORT MEDICAL PLC, Hertfordshire (GB)

( * ) Notice: Subject to any disclaimer, the term of this patent is extended or adjusted under 35 U.S.C. 154(b) by 603 days.

(21) Appl. No.: 15/033,133

(22) PCT Filed: Nov. 3, 2014

(86) PCT No.: PCT/GB2014/053253
§ 371 (c)(1),
(2) Date: Apr. 29, 2016

(87) PCT Pub. No.: WO2015/063509
PCT Pub. Date: May 7, 2015

(65) Prior Publication Data
US 2016/0263323 A1 Sep. 15, 2016

(30) Foreign Application Priority Data

Nov. 1, 2013 (GB) .................................. 1319377.6

(51) Int. Cl.
*A61M 5/20* (2006.01)
*A61M 5/32* (2006.01)
(Continued)

(52) U.S. Cl.
CPC ............ *A61M 5/20* (2013.01); *A61M 5/2053* (2013.01); *A61M 5/3148* (2013.01);
(Continued)

(58) Field of Classification Search
CPC .. A61M 5/155; A61M 5/2046; A61M 5/3015; A61M 5/2053;
(Continued)

(56) References Cited

U.S. PATENT DOCUMENTS 4,790,824 A * 12/1988 Morrow .................. A61M 5/30
604/143
7,744,563 B2 * 6/2010 Landau .................... A61M 5/30
604/68
2003/0114789 A1 6/2003 Haar et al.

FOREIGN PATENT DOCUMENTS

GB 2283918 A 5/1995
JP 2001521791 A 11/2001
(Continued)

OTHER PUBLICATIONS

Patent Cooperation Treaty, International Search Report, dated Mar. 31, 2015, European Patent Office.
(Continued)

*Primary Examiner* — Bhisma Mehta
*Assistant Examiner* — Hong-Van N Trinh
(74) *Attorney, Agent, or Firm* — Taft Stettinius & Hollister LLP; Stephen F. Rost

(57) ABSTRACT

A sub-assembly for a medicament delivery device including a housing, a propellant source contained in and axially moveable relative to said housing, and a button axially moveable relative to said housing. At least part of said button is disposed axially rearwardly of part of said propellant source. The button includes one or more radially flexible blocking members, and the button is moveable between a first axial position in which the one or more radially flexible blocking members are radially restrained by the housing in a radially inward position that limits rearward axial movement of the propellant source, and a second axial position in which the one or more radially flexible blocking members
(Continued)

are able to flex to a radially outward position and permit rearward axial movement of the propellant source relative to the button and the housing.

22 Claims, 10 Drawing Sheets

(51) Int. Cl.
 *A61M 5/31* (2006.01)
 *A61M 5/46* (2006.01)
(52) U.S. Cl.
 CPC .......... *A61M 5/3204* (2013.01); *A61M 5/326* (2013.01); *A61M 5/3202* (2013.01); *A61M 5/46* (2013.01); *A61M 2005/2026* (2013.01); *A61M 2005/3247* (2013.01); *A61M 2005/3267* (2013.01)
(58) Field of Classification Search
 CPC .... A61M 2005/14204; A61M 5/31585; A61M 5/3158; A61M 5/20; A61M 5/326; A61M 2005/2026; A61M 5/30; A61M 5/31511; A61M 5/315; A61M 5/2033; A61M 2005/2073; A61M 5/145; A61M 5/1452; A61M 5/14526

See application file for complete search history.

(56) References Cited

FOREIGN PATENT DOCUMENTS

| | | | |
|---|---|---|---|
| JP | 2013534164 A | 9/2013 |
| WO | 2002011791 A1 | 2/2002 |
| WO | 2005070483 A1 | 8/2005 |
| WO | 2009086250 A1 | 7/2009 |
| WO | 2011101379 A1 | 8/2011 |
| WO | 2011162686 A1 | 12/2011 |
| WO | 2014066461 A1 | 5/2014 |

OTHER PUBLICATIONS

Patent Cooperation Treaty, Written Opinion of the International Searching Authority, dated Mar. 31, 2015, European Patent Office.
United Kingdom Search Report for Priority Application GB 1319377. 6, dated Jun. 10, 2014.
Office Action, Japan Patent Office, Japanese Application No. 2016-551073, dated Jul. 24, 2018, 4 pages.

* cited by examiner

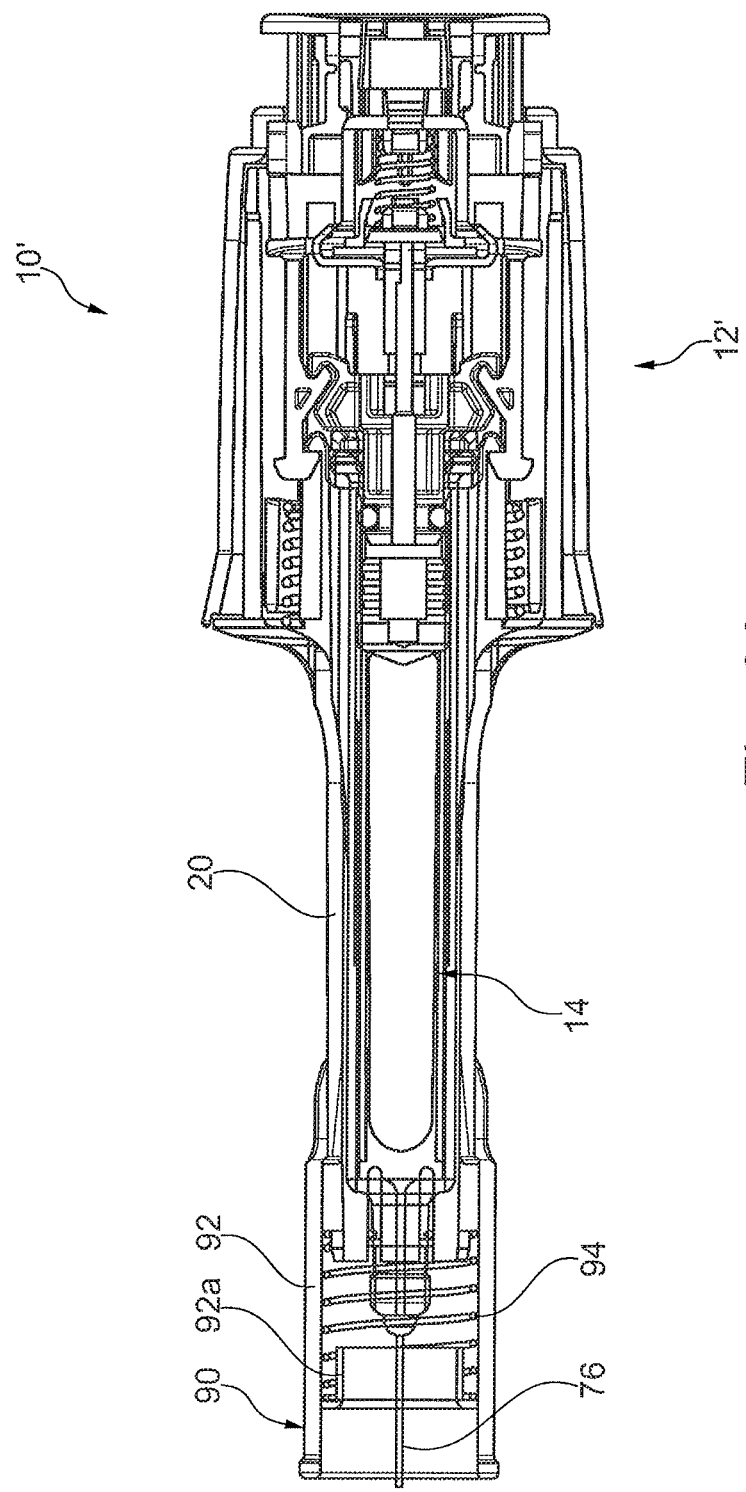

MEDICAMENT DELIVERY DEVICE SUB-ASSEMBLY

This invention relates to a medicament delivery device, and in particular, to a sub-assembly of a medicament delivery device for receiving a syringe.

BACKGROUND

Known medicament delivery devices include autoinjector devices and in certain instances consist of a sub-assembly and a syringe that is installed in the sub-assembly. Some of these prior art arrangements have the advantage of permitting the use of standard specification syringes in a delivery device irrespective of the syringe manufacturer, thereby obviating the need for pharmaceutical companies to provide filled syringes specific to a particular device.

It is an object of at least one embodiment of the present invention to provide a sub-assembly for a medicament delivery device that overcomes at least some of the disadvantages associated with prior art arrangements.

BRIEF SUMMARY OF THE DISCLOSURE

In accordance with a first aspect of the present invention there is provided a sub-assembly for a medicament delivery device, the sub-assembly comprising:
 a housing;
 a propellant source contained in and axially moveable relative to said housing; and
 a button axially moveable relative to said housing, at least part of said button being disposed axially rearwardly of part of said propellant source;
 wherein the button includes one or more radially flexible blocking members, and the button is moveable between a first axial position in which the one or more radially flexible blocking members are radially restrained by the housing in a radially inward position that limits rearward axial movement of the propellant source, and a second axial position in which the one or more radially flexible blocking members are able to flex to a radially outward position and permit rearward axial movement of the propellant source relative to the button and the housing.

The one or more radially flexible blocking members may be moveable from the radially inward position to the radially outward position by a rearwardly axial force acting on the one or more radially flexible blocking members when in the second axial position. The one or more radially flexible blocking members may have a tapered front surface such that the one or more radially flexible blocking members are moveable from the radially inward position to the radially outward position by a rearwardly axial force acting on the tapered front surface when in the second axial position.

The housing may include a rear housing and a front housing, and axially rearward movement of the propellant source relative to the housing causes a retraction biasing member to delatch, wherein the delatched retraction biasing member urges the rear housing axially rearwardly relative to the front housing. The retraction biasing member is delatched when latch heads are moved from a radially inward position to a radially outward position. The axially rearward movement of the propellant source relative to the housing permits axially rearward movement of a plug, wherein axially rearward movement of the plug urges the latch heads from the radially inward position to the radially outward position. The latch heads may be disposed on radially flexible legs, and wherein the plug includes hooks that are engageable with the radially flexible legs so as to prevent the legs flexing radially outwardly, the hooks being capable of disengaging legs when the plug moves axially rearwardly relative to the legs.

The latch heads may be formed on an inner housing and the latch heads are axially aligned with first stops of the front housing when in the radially outward position, and wherein abutment between the latch heads and first stops prevents axially rearward movement of the inner housing relative to the front housing.

One of the front housing and rear housing may include second stops and the other of the front housing and rear housing includes lock out elements, wherein engagement between the second stops and lock out elements prevents forwardly and rearwardly axial movement of the rear housing relative to the front housing, and wherein the second stops are engageable in the lock out elements when the rear housing is axially rearwardly displaced relative to the front housing by a predetermined axial distance.

The sub-assembly may further comprise one or more latches on one of the button or the housing, wherein the one or more latches engage the other of the button or the housing when the button is in the second axial position, and wherein engagement of the one or more latches prevents axially rearward movement of the button relative to the housing.

The sub-assembly may further comprise a needle sleeve wherein the needle sleeve is axially moveable relative to the housing between a forward axial position and a rearward axial position, wherein in the rearward axial position the needle sleeve determines maximum axial length of a needle extending therethrough relative to the needle sleeve. The sub-assembly may further include a biasing member that biases the needle sleeve towards the forward axial position relative to the housing.

A forward surface of the sub-assembly may be inclined relative to a longitudinal axis of the sub-assembly, wherein the angle of inclination of the forward surface determines the angle at which the sub-assembly may be held against a delivery site to achieve maximum penetration of a needle extending from the sub-assembly.

Alternatively, the sub-assembly may include a series of points that are each the axially most forward point of the sub-assembly at a given radii, and wherein the series of points lie in a plane that is inclined relative to a longitudinal axis of the sub-assembly, wherein the angle of inclination of the plane determines a minimum angle at which a needle of a syringe mounted in the sub-assembly may be inserted into a delivery site.

The propellant source may comprise a reservoir housing defining a reservoir for containing propellant, and a stem having a bore therethrough, at least one inlet in fluid communication with the bore, and an open outlet end in fluid communication with the bore, the stem being moveable relative to the reservoir housing between a first position in which the at least one inlet is not in fluid communication with the reservoir and a second position in which the at least one inlet is in fluid communication with the bore. The propellant source may further comprise a biasing member for biasing the stem towards the first position. The reservoir may contain a liquefied gas propellant, and/or may contain a propellant that is or contains a hydrofluoroalkane (HFA), wherein the propellant may be or contain HFA134a.

In accordance with a first aspect of the present invention there is provided a medicament delivery device comprising a sub-assembly according to the first aspect of the present invention and a syringe connected to the sub-assembly, wherein the syringe includes a barrel for containing medicament, the barrel having an outlet at a front end, and a stopper axially moveable in the barrel.

The syringe may further include a needle in fluid communication with the outlet.

The syringe may be axially restrained relative to the rear housing such that axial movement of the rear housing relative to the front housing causes axial movement of the syringe relative to the front housing.

BRIEF DESCRIPTION OF THE DRAWINGS

Embodiments of the invention are further described hereinafter with reference to the accompanying drawings, in which:

FIG. 8A is a cross-sectional view of a medicament delivery device in accordance with an alternative embodiment of the present invention including a needle sleeve in a needle-protecting position.

DETAILED DESCRIPTION

Figure 1:
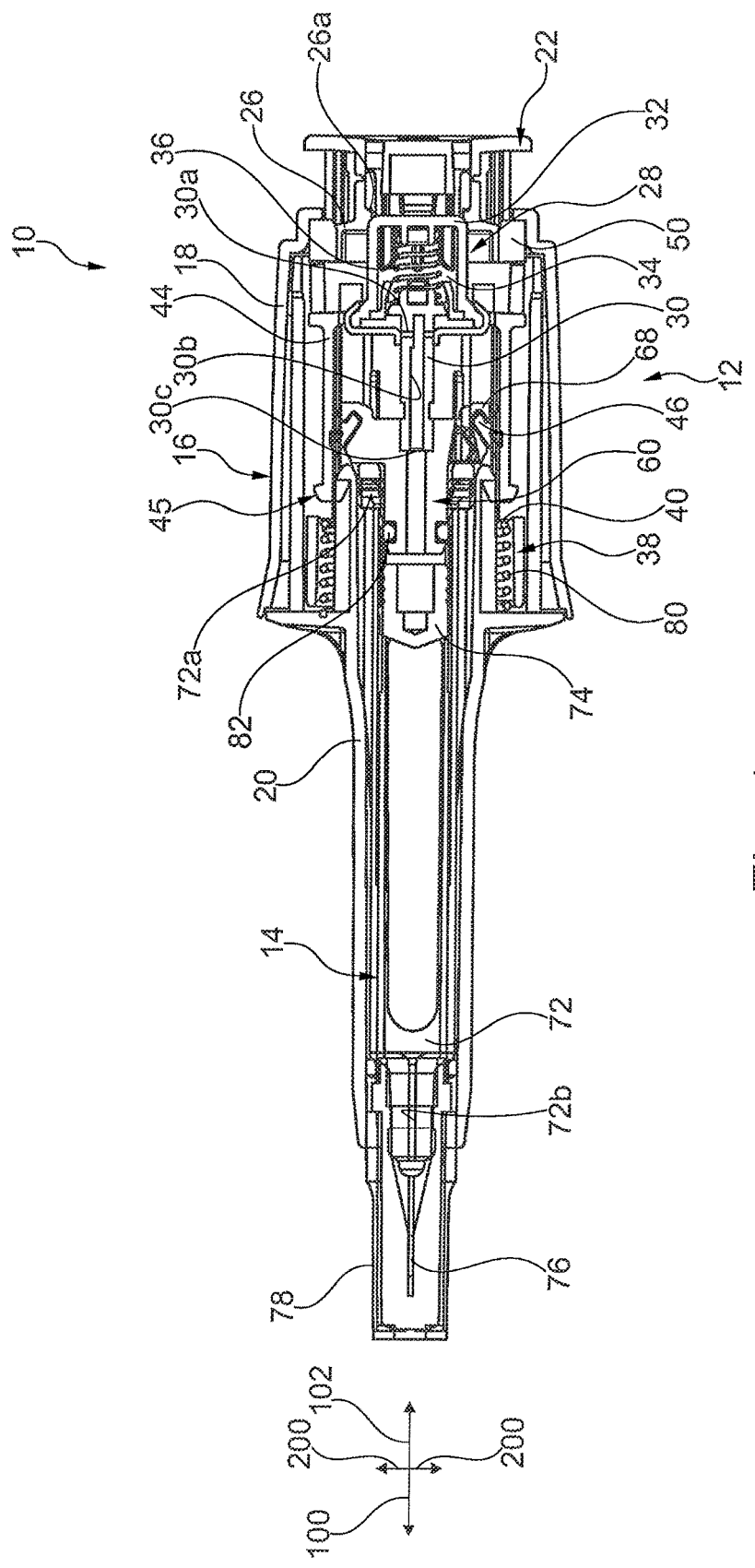
FIG. 1 is a cross-sectional view of a medicament delivery device in accordance with an embodiment of the present invention.

FIG. 1 shows a cross-sectional view of a medicament delivery device 10 in accordance with an embodiment of the present invention. The medicament delivery device 10 comprises a sub-assembly 12 and a syringe 14 assembled in the sub-assembly 12. The syringe 14 has a syringe barrel 72 having a flange 72a at a rear end, a stopper 74 disposed in the syringe barrel 72 and axially slidable therein, and a needle 76 in fluid communication with a fluid outlet 72b of the syringe 14. The syringe 14 is configured to contain a medicament and permit delivery of the medicament to a delivery site when the stopper 74 moves axially forwardly in the syringe barrel 72 and causes medicament to be expelled through the needle 76 via the fluid outlet 72a. Initially, a needle shield 78 may surround the needle 76 prior to its use, as shown in FIG. 1, to prevent injury during handling of the device 10.

The device 10 extends in an axial direction along a longitudinal axis. The forward axial direction is indicated by arrow 100 in FIG. 1 and the rearward axial direction is indicated by arrow 102. Radial directions are indicated by arrows 200 and are relative to the longitudinal axis (i.e. the axial line through the centre of the device).

The sub-assembly 12 includes a housing 16 formed of a front housing 20, a rear housing 18 and an inner housing 38. The inner housing 38 is attached to the rear housing 18 (e.g. by a press-fit or interference fit). The sub-assembly 12 further includes a button 22 disposed at a rear end of the device 10 and being axially moveable relative to the housing 16, a propellant source 28 and a plug 60. The propellant source 28 includes a reservoir housing 32 defining a reservoir 34 for containing a volume of propellant and a stem 30. The stem 30 includes a bore 30b therethrough, an inlet 30a in fluid communication with the bore 30b and an outlet 30c at a front end that is also in fluid communication with the bore 30b. The stem 30 is axially moveable relative to the propellant housing 32 from a position in which the inlet 30a is not in fluid communication with the reservoir 34 to a position in which the inlet 30a is in fluid communication with the reservoir 34. In the non-limiting embodiment shown in the Figures, the propellant source 28 additionally contains a biasing member 36 (e.g. a spring) that biases the stem 30 to the position in which the inlet 30a is not in fluid communication with the reservoir 34. In the absence of a biasing member, the stem 30 may be retained in the position in which the inlet 30a is not in fluid communication with the reservoir 34 by the pressure of the propellant in the reservoir 34. Furthermore, in certain embodiments, the propellant source 28 preferably includes a latching mechanism whereby the stem 30 is latched in the position in which the inlet 30a is in fluid communication with the reservoir 34 once the stem 30 is moved axially rearwardly relative to the reservoir housing beyond a predetermined axial point.

Figure 2:
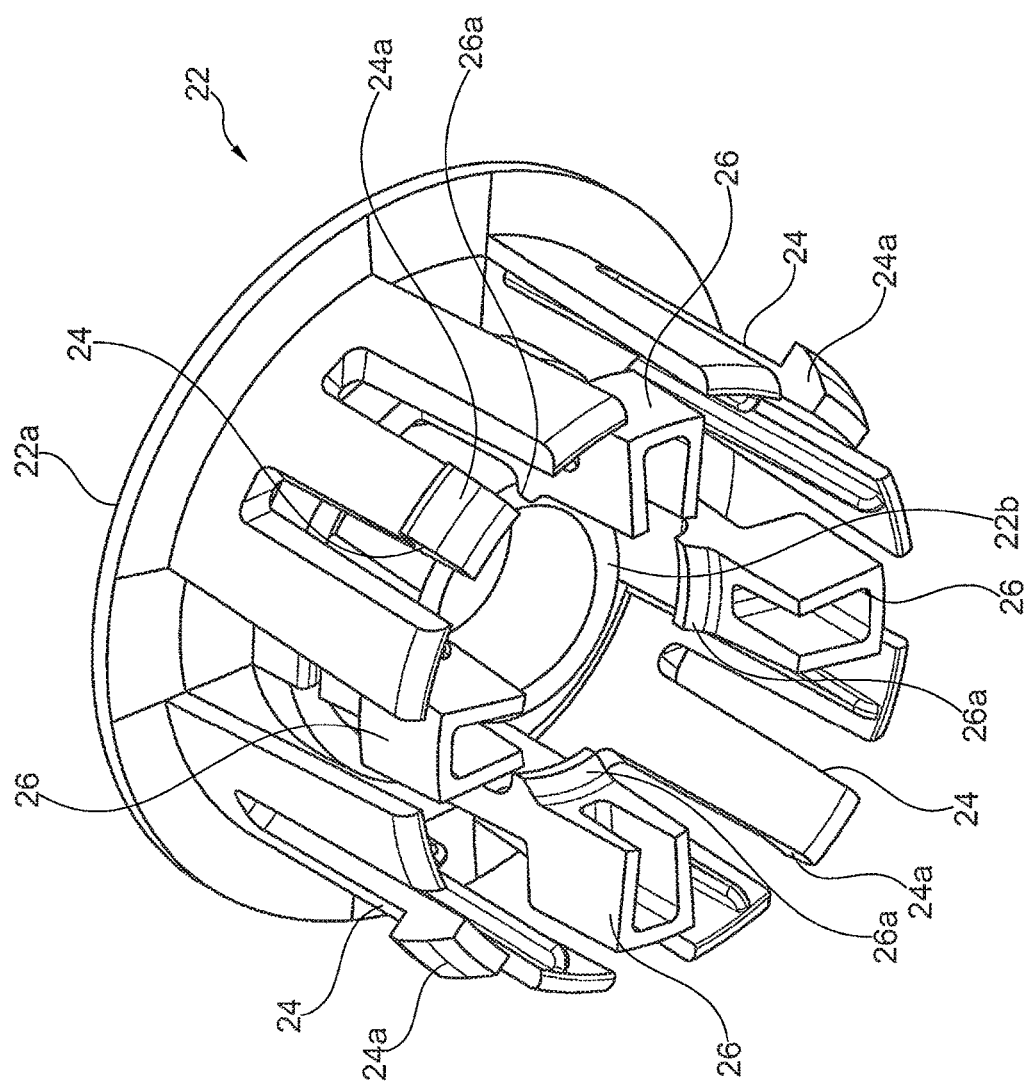
FIG. 2 is a perspective view of the button of the medicament delivery device of FIG. 1.
Figure 3:
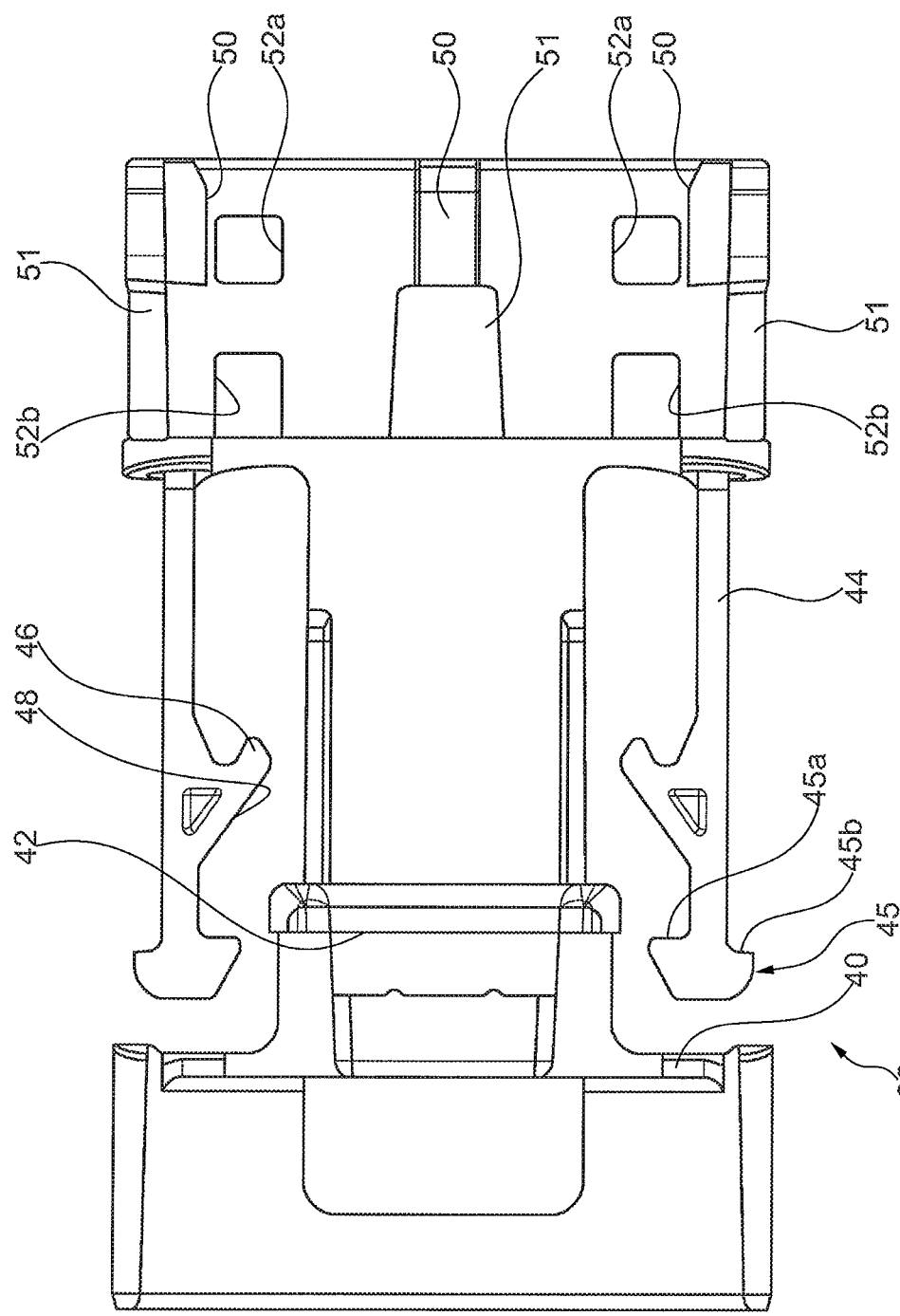
FIG. 3 is a cross-sectional view of the inner housing of the medicament delivery device of FIG. 1.

The button 22 is shown in more detail in FIG. 2 in which it can be seen to include a rear wall 22a (which is disc-like in the non-limiting embodiments shown in the Figures), a plurality of latches 24 extending axially forwardly from the rear wall 22a and a plurality of blocking members 26 extending axially forwardly from the rear wall 22a. Each of the plurality of latches 24 is radially flexible and includes a radially projecting foot 24a and has a tapered front surface. The latches 24 are arranged to latch the button 22 to a part of the housing 16 to prevent rearwardly axial movement of the button 22 relative to the housing 16 such that the button 22 is not removable from the housing 16 and may be held in a depressed state relative to the housing 16 after depression. The latches 24 may latch to any part of the housing 16. In the non-limiting specific embodiment shown in the Figures, the latches 24 latch to the inner housing 38, and specifically, the feet 24a of the latches 24 initially locate in rear apertures 52a (as shown in FIG. 3) of the inner housing 38. The latches 24 may flex radially inwardly when the button 22 is depressed, and move axially forwardly where the latches 24 locate in forward apertures 52b and prevent subsequent rearward axial movement of the button 22 relative to the inner housing 38.

Each of the plurality of blocking members 26 is radially flexible and has a radially inwardly projecting lip 26a. In combination, the plurality of lips 26a form a discontinuous radially inwardly projecting flange.

In the non-limiting embodiment shown in the Figures, the plurality of blocking members 26 are disposed radially inward of the plurality of latches 24 when each is in a relaxed unbiased state.

Additionally, the button 22 includes a boss 22b extending axially forwardly from the rear wall 22a, radially inward of the blocking members 26.

The inner housing 38 is shown in more detail in FIG. 3. As can be seen from FIG. 3, the inner housing 38 is generally cylindrical and has a first reaction surface 40 and a second reaction surface 42, where the first reaction surface 42 is radially outward of the second reaction surface 42 and each of the first reaction surface 42 and second reaction surface 42 has a central aperture therethrough. The second reaction surface 42 provides an axially limiting abutment surface for the flange 72a of the syringe 14, and, as is described in more detail below, the first reaction surface 40 provides an abutment surface for a retraction spring 80 to act against.

The inner housing 38 includes a pair of radially flexible legs 44 that extend in an axially forwardly direction. The legs 44 each have a head 45 at a forward end where each head 45 has a radially inward part 45a and a radially outward part 45b. The legs 44 also include a catch 46 that projects both radially inwardly and axially rearwardly. The legs 44 additionally include a tapered portion 48 that tapers radially inwardly in an axially forwardly direction (i.e. the radial extent of the tapered portion 48 becomes less so in an axially forwardly direction) for facilitating urging of the legs 44 in a radially outward direction when a rearward axial force is applied to the tapered portion 48.

Towards the rear end of the inner housing 38, the inner housing 38 includes the apertures 52 described above for receiving the feet 24a of the latches 24 of the button 22. Additionally, the inner housing 38 includes a plurality of blocks 50 that project radially inwardly, and a plurality of windows 51 that are each axially aligned with and axially forwardly of one of the blocks 50. The circumferential distribution of the blocks 50 and windows 51 corresponds to the circumferential distribution of the blocking members 26 of the button 22.

Figure 4:
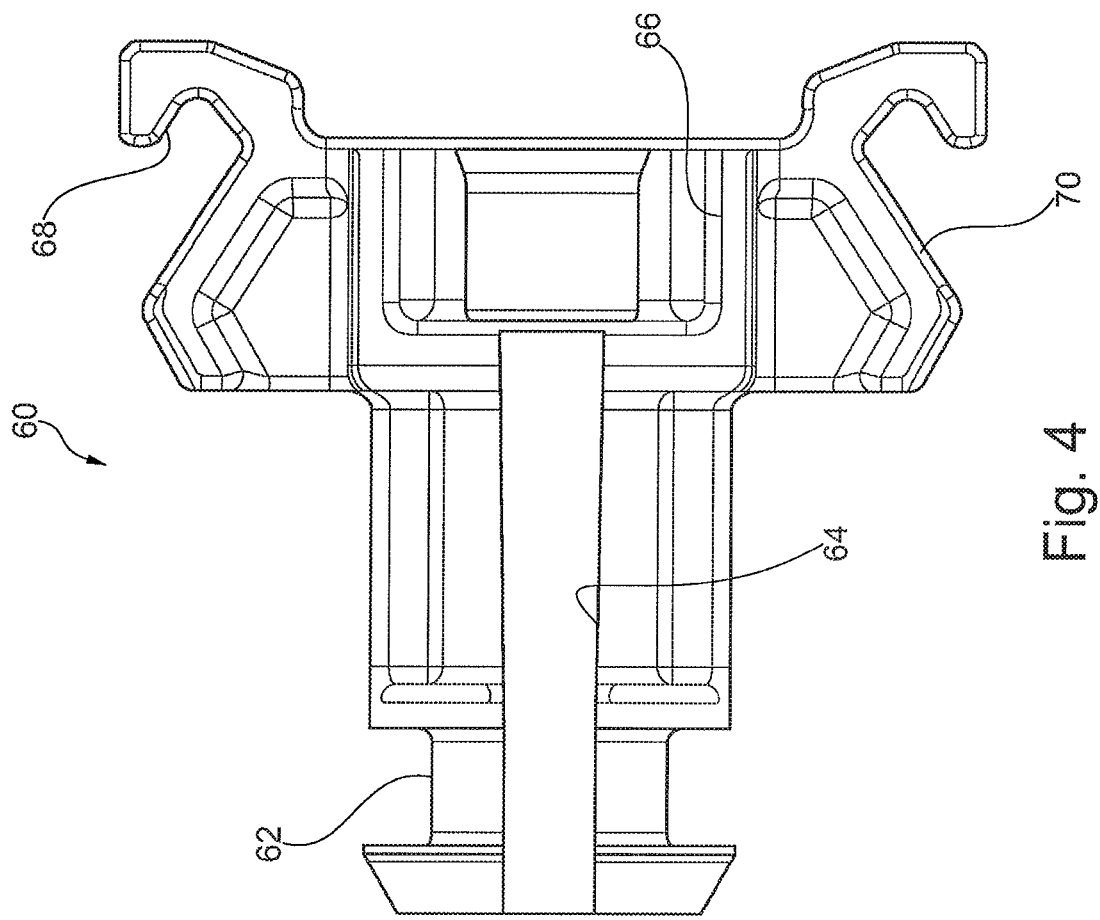
FIG. 4 is a cross-sectional view of the plug of the medicament delivery device of FIG. 1.

FIG. 4 shows the plug 60 in detail. The plug includes a central bore 64 running therethrough, and, in the embodiment shown in the Figures, has a groove 62 about its external surface for receiving a seal 82 (e.g. an O-ring seal) for sealing the plug 60 to the inside a the syringe barrel 72. A rear end of the plug 60 includes a socket 66 for receiving and radially restraining the stem 30 of the propellant source 28. The plug 60 includes a pair of hooks 68 that extend radially outwardly and axially forwardly, and additionally includes a pair of wings 70 that extend radially outwardly. Rear surfaces of the wings 70 are preferentially tapered radially inwardly in an axially rearwardly direction as shown in the Figures.

Returning to FIG. 1 which shows the device 10 prior to use, the retraction spring 80 is initially in a compressed state between the front housing 20 and the first reaction surface 40 of the inner housing 38. The inner housing 38 is prevented from moving axially rearwardly under the influence of the retraction spring 80 due to abutment between the heads 45 and the front housing 20. The hooks 68 of the plug 60 radially restrain the catches 46 of the inner housing 38 so as to prevent the legs 44 flexing radially outwardly and permitting the heads 45 to disengage from the front housing 20 and permit the inner housing 38 to move axially rearwardly relative to the front housing 20 under the influence of the retraction spring 80. The plug 60 is partly disposed in the syringe barrel 72 and the stem 30 of the propellant source 28 is located in the socket 66 of the plug 60.

To actuate the device 10, the needle shield 78 is removed to expose the needle 76 and the needle 76 is inserted into a delivery site. The button 22 is then depressed (i.e. moved axially forwardly relative to the housing 16). Depression of the button 22 causes the propellant reservoir 32 to move axially forwardly, and, due to forwardly axial restraint of the stem 30 (i.e. via the plug 60 that is forwardly axially restrained by the syringe flange 72a which, in turn, is forwardly axially restrained by the front housing 20), the propellant housing 32 moves axially forwardly relative to the stem 30 thereby bringing the inlet 30a into fluid communication with the reservoir 34. In particular, the blocks 50 radially restrain the blocking members 26 of the button 22 as the button 22 is moved axially forwardly such that the lips 26a remain axially aligned with the propellant housing 32 and cause the propellant housing 32 to move axially forwardly relative to the stem 30. In the preferable embodiment shown in the Figures, the feet 24a of the latches 24 latch into forward apertures 52b of the inner housing 38 causing the button 22 to be axially restrained in a depressed configuration relative to the housing 16.

Figure 5:
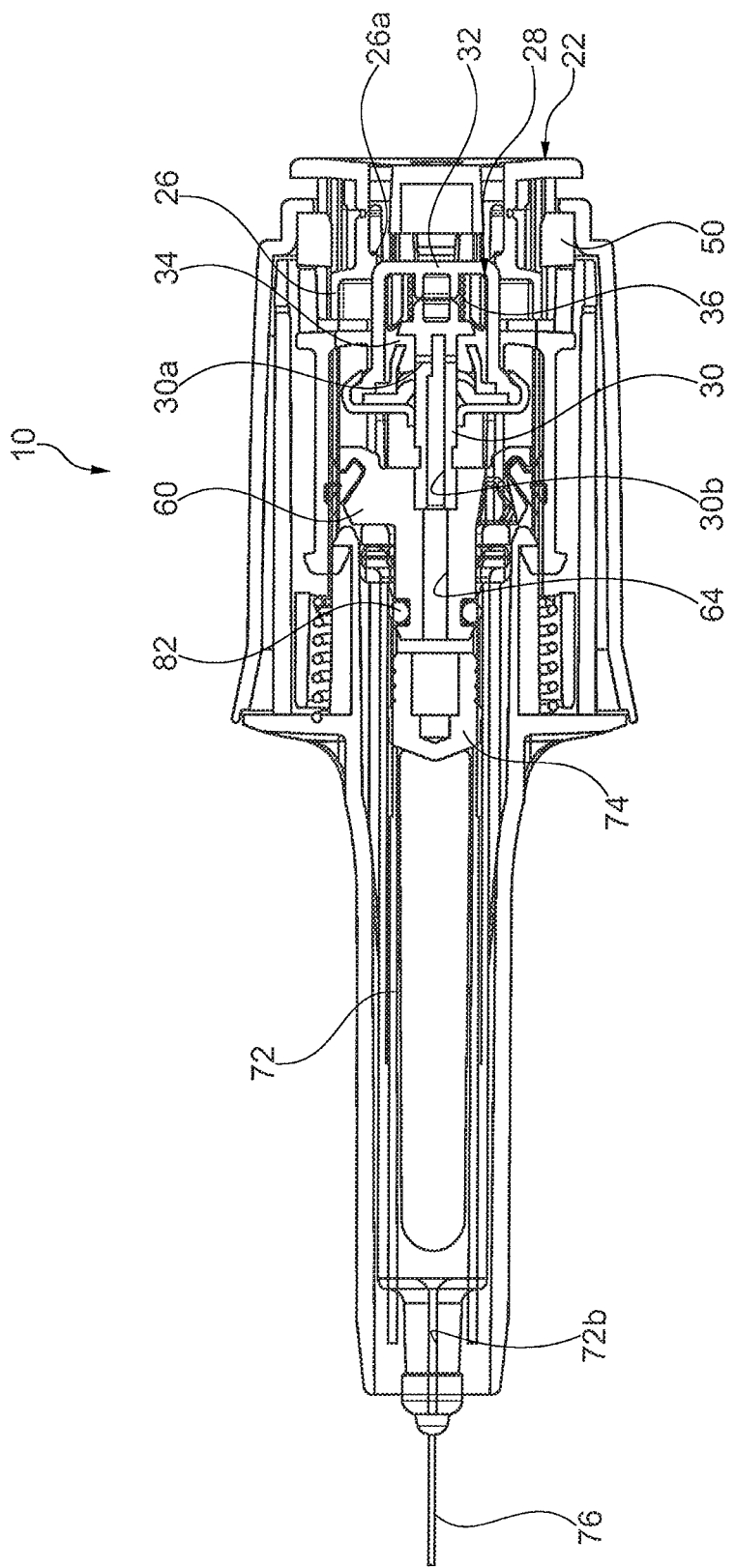
FIG. 5 is a cross-sectional view of the medicament delivery device of FIG. 1 during delivery of a dose of medicament.
Figure 6:
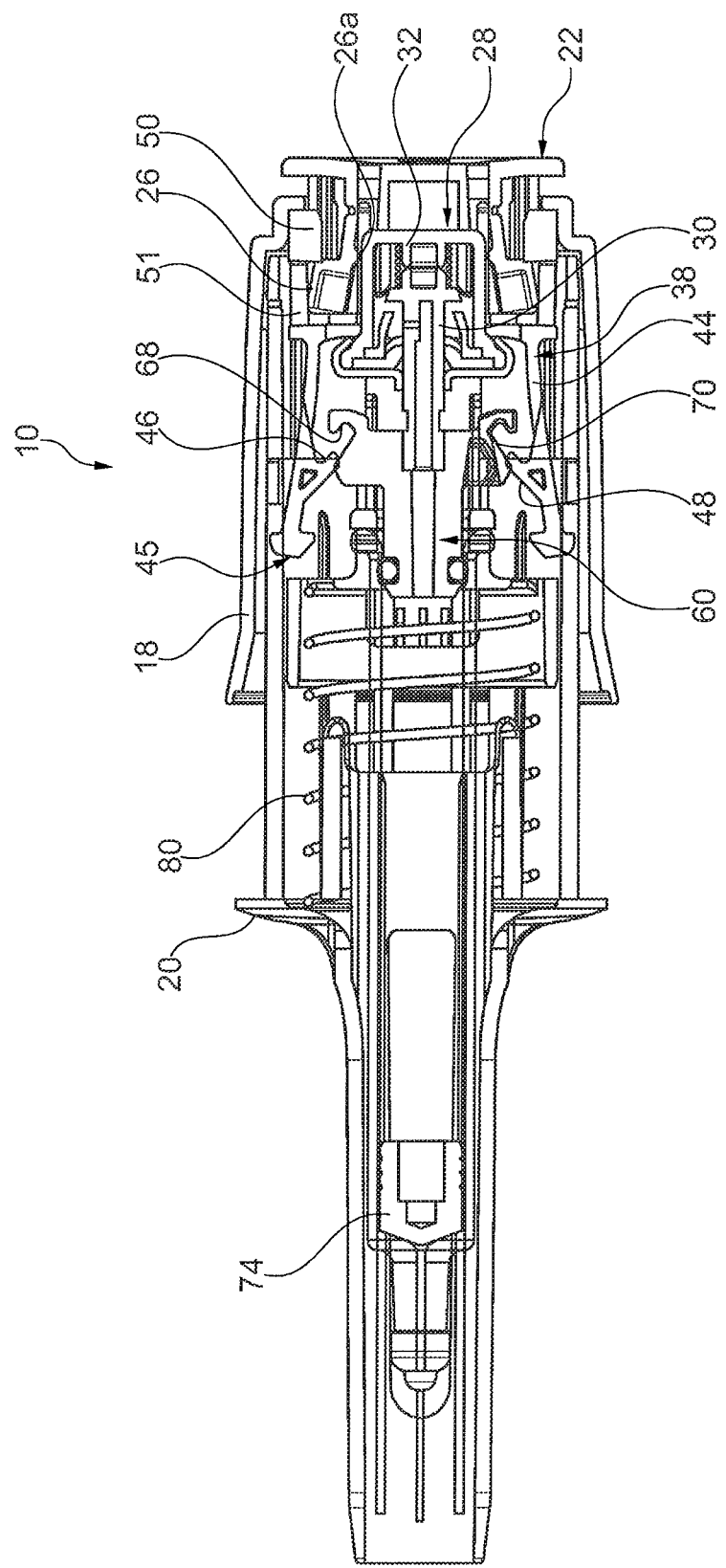
FIG. 6 is a cross-sectional view of the medicament delivery device of FIG. 1 following retraction of the syringe into the front housing.

FIG. 5 shows the device 10 with the button 22 depressed and the inlet 30a of the stem 30 in fluid communication with the reservoir 34. In this configuration, propellant may flow from the reservoir 32 to the syringe barrel 74 via the bore 30b of the stem 30 and the bore 64 of the plug 60. In particular, propellant is supplied to the syringe barrel 72 and provides a vapour pressure in the sealed volume between the stopper 74 and the seal 82 surrounding the plug 60. In particularly preferable embodiments, the propellant exits the reservoir 34 as a liquid and vapourises to provide a vapour pressure. As the vapour pressure increases, the friction between the stopper 74 and the barrel 72 (and other resistive forces) is overcome and the stopper 74 begins to move axially forwardly in the barrel 72 (and any other forces opposing the axial motion of the seal 82 and plug 60). A medicament contained axially forwardly of the stopper 74 in the barrel 72 is then pressurized and forced out of the outlet 72b of the syringe 14 into the delivery site via the needle 76. The rising vapour pressure between the stopper 74 and seal 82 additionally causes the plug 60 and seal 82 to move axially rearwardly in the barrel 72 when the force provided by the pressure is sufficient to overcome the friction between the seal 82 and the barrel 72. The axially rearwardly moving plug 60 causes the stem 30 to move axially rearwardly and applies an axially rearwardly force to the propellant housing 32 and the lips 26a of the blocking members 26. Due to the curved edges of the reservoir housing 32 contacting the lips 26a and the tapered forward surfaces of the lips 26a, the force axially rearwardly applied to the lips 26a urges the blocking members 26 radially outwards so as to permit the axially rearward movement of the propellant source 28 relative to the button 22 (and the housing 16). Thus, the plug 60 and propellant source 28 move axially rearwardly in the housing 16. The blocking members 26 are able to move radially outwardly because they have moved to an axial position (when the button 22 was pressed) in which the blocking members 26 are no longer radially restrained by blocks 50. The blocking members 26 may flex radially outwardly into the windows 51, or any suitable recess that permits radial movement of the blocking members 26. The boss 22b of the button 22 limits the extent of the axially rearward movement of the plug 60 such that the plug 60 is unable to move out of the syringe barrel 72.

Figure 7A:
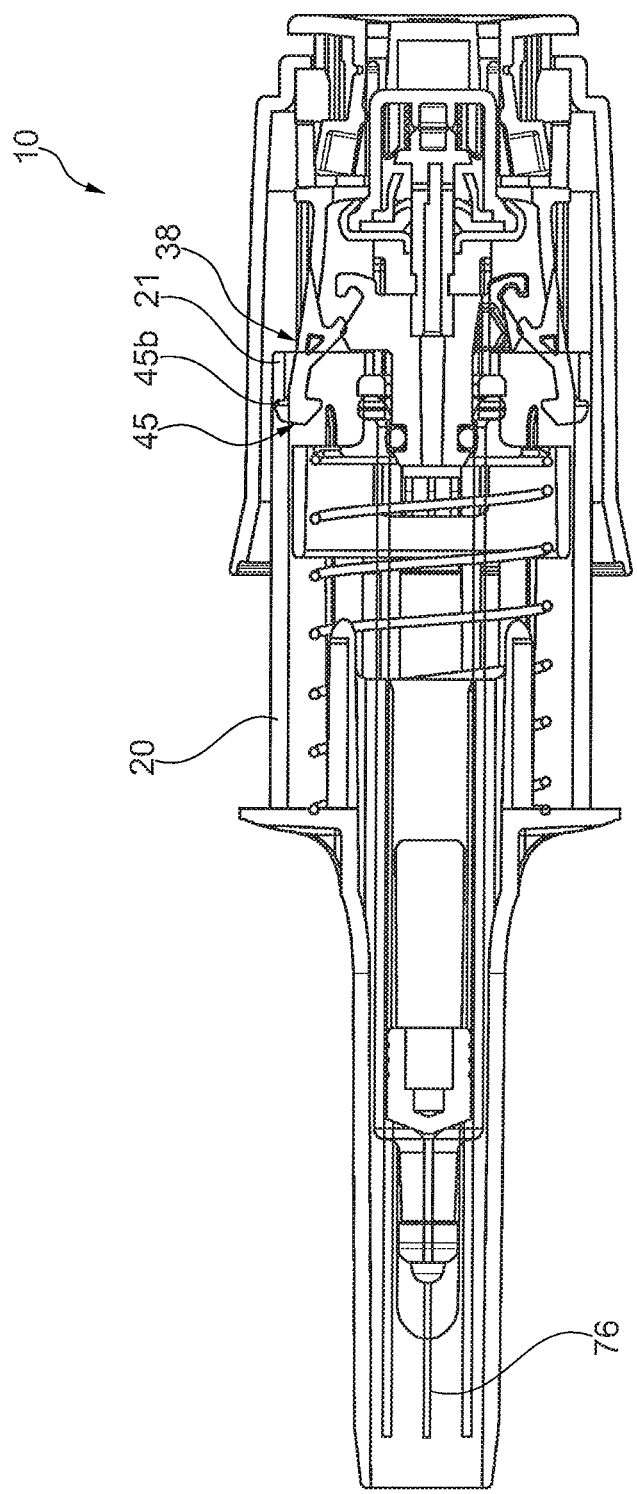
FIG. 7A is a cross-sectional view of the medicament delivery device of FIG. 1 following retraction of the syringe into the front housing with the inner housing latched against the front housing.
Figure 7B:
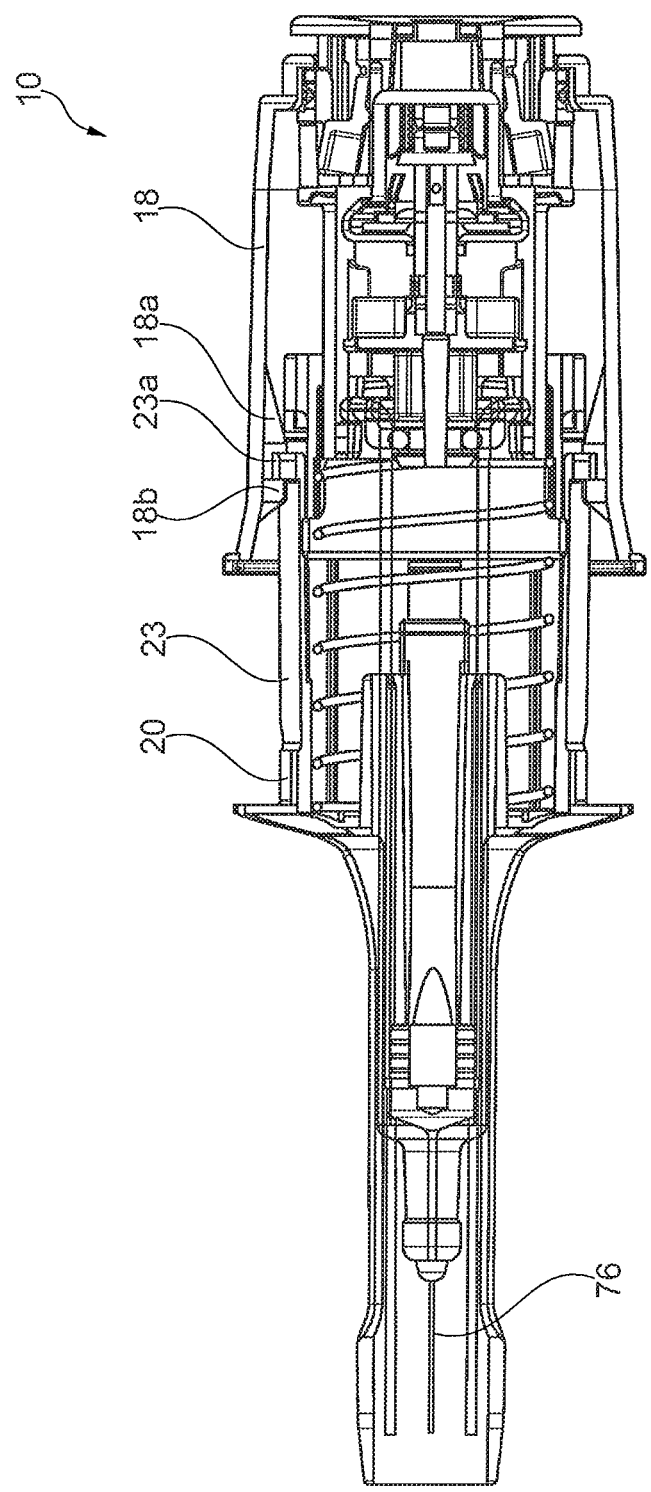
FIG. 7B is a cross-sectional view of the medicament delivery device of FIG. 7A rotated 90° about the longitudinal axis and showing the rear housing latched against the front housing.

As the plug moves axially rearwardly, the hooks 68 move to a position in which they are no longer radially aligned with catches 46 and so no longer prevent outwardly radial flexing of the legs 44. Concurrently, wings 70 act against tapered portions 48 and urge the legs 44 radially outwardly causing heads 45 to disengage from the front housing 20. Once the heads 45 are no longer engaged with the front housing 20, only a user-applied axially forward force on the rear housing 18 (to which the inner housing 38 is connected)

prevents the retraction spring 80 from causing the inner housing 38 (and rear housing 18) to move axially rearwardly relative to the front housing 20. When the user does release the axially forward force applied to the rear housing 18 (e.g. at the end of medicament delivery, or possibly part way through), the inner housing 38 and rear housing 18 move axially rearwardly relative to the front housing 20. In doing so, the propellant source 28, plug 60 and syringe 14 are also caused to move axially rearwardly relative to the front housing 20. Consequently, the previously exposed needle 76 of the syringe 14 is drawn axially into the front housing 20 to a non-exposed configuration (as shown in FIGS. 7A and 7B). Axially rearward travel of the inner housing 38 (and hence rear housing 18, propellant source 28, plug 60 and syringe 14) relative to the front housing 20 is arrested when heads 45 (specifically, radially outward parts 45*b* of the heads in the embodiment shown in the Figures), which are in a radially outwardly flexed position, abut first stops 21 of the front housing 20 (as shown in FIG. 7A).

FIG. 7B shows the device 10 of FIG. 7A in the same configuration but rotated 90° about the longitudinal axis. As shown in FIG. 7B, the rear housing 18 includes rear lock out elements 18*a* and front lock out elements 18*b* on an inner surface of the rear housing 18. The rear lock out elements 18*a* are tapered on a rear surface such that the rear lock out elements 18*a* extend gradually more radially inwardly in an axially forwardly direction. Conversely, front surfaces of the rear lock out elements 18*a* extend in a substantially radial direction only. Front lock out elements 18*b* each have a rear surface that extends in a substantially radial direction only and is axially forward of and axially spaced from the front surfaces of the rear lock out elements 18*a*.

The front housing 20 additionally includes second stops 23*a* that are formed on radially flexible arms 23.

As the rear housing 18 moves axially rearwardly relative to the front housing 20, rear lock out elements 18*a* ride axially over second stops 23*a* and cause the radially flexible arms 23 to flex radially inwardly. Once the second stops are axially forward of the rear lock out elements 18*a*, the arms 23 relax and flex radially outwardly such that the second stops 23*a* are axially restrained between front lock out elements 18*b* and rear lock out elements 18*a*. Consequently, the rear housing 18 is axially restrained both forwardly and rearwardly relative to the front housing 20. Whilst the axial restraint of the second stops 23*a* between the front lock out elements 18*b* and the rear lock out elements 18*a* serves as the primary "lock-out" mechanism for preventing axial movement of the rear housing 18 relative to the front housing 20, the abutment of the heads 45 against first stops 21 serves as a secondary "lock-out" mechanism. These two lock-out mechanisms result in the device being fixed in a "needle safe" configuration, where the needle 76 is covered by the front housing 20 and is prevented from being moved out therefrom.

Figure 8B:
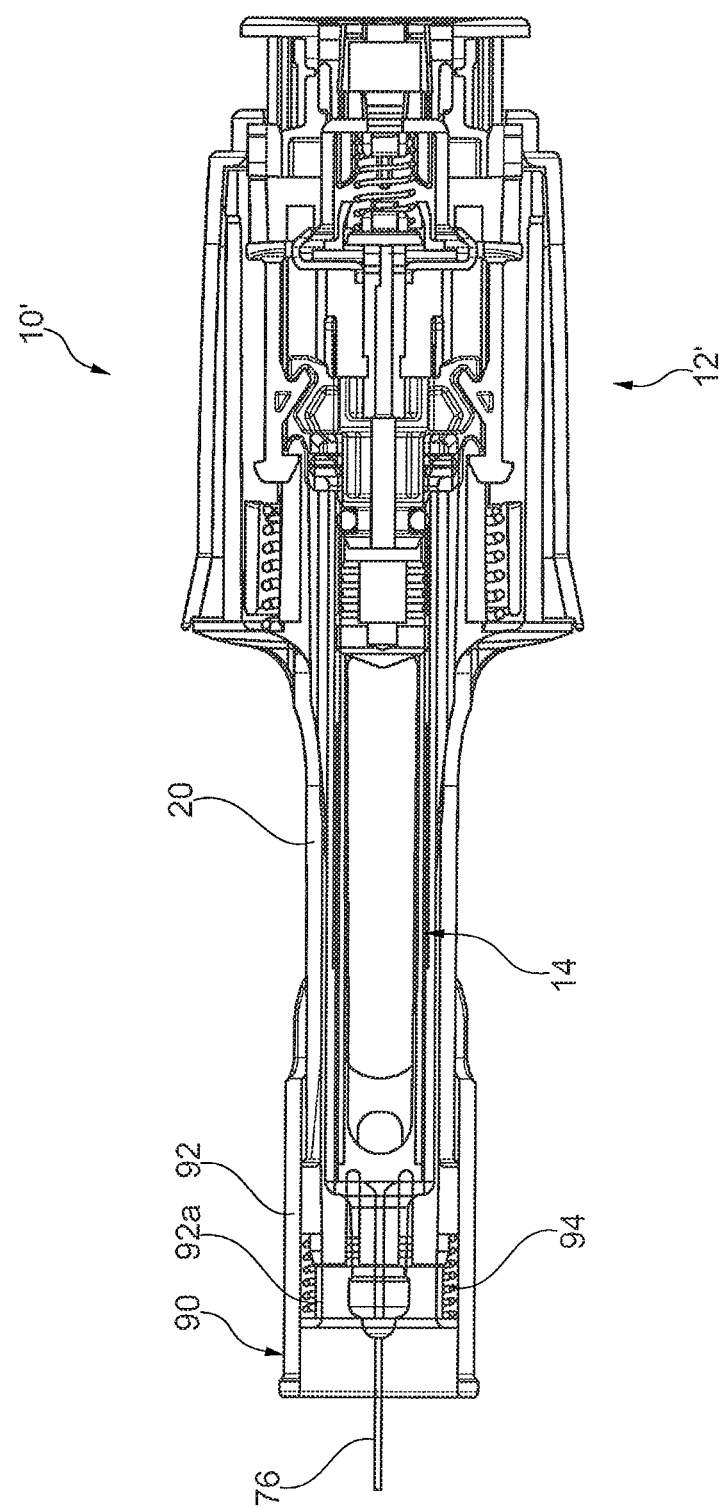
FIG. 8B is a cross-sectional view of the medicament delivery device of FIG. 8A with the needle sleeve in a needle-exposing position.

An alternative embodiment of a medicament delivery device 10' is shown in FIGS. 8A and 8B and includes a modified sub-assembly 12' that has a retractable needle sleeve 90 connected to the front end of the front housing 20. The needle sleeve 90 includes a sleeve 92 and a spring 94 (or alternative biasing member) that biases the sleeve axially forwardly into a position in which the needle 76 is covered or mostly covered by the sleeve 92. The sleeve 92 is rearwardly axially moveable relative to the needle 76 so as to expose the needle 76 upon compression of the spring 94. FIG. 8A shows the needle shield 90 in a needle protecting position and FIG. 8B shows the needle shield 90 in a needle exposed position. In use, the needle shield 90 may be moved from the needle protecting position to a needle exposed position by pushing the device 10' axially forwardly against a delivery site (in which case the needle 76 will be exposed relative to the needle sleeve 90 but will penetrate the delivery site so will remain entirely hidden from the user). In the embodiment shown in FIGS. 8A and 8B, the sleeve 92 includes a boss 92*a* that abuts a front end of the front housing 20 when moved axially rearwardly relative thereto. This abutment limits the axial rearward movement of the sleeve 92 relative to the front housing 20 and consequently determines the maximum axial length of the needle 76 beyond the sleeve 92. Such an arrangement limits the extent to which the needle 76 may penetrate a delivery site. Any suitable limiting member between the sleeve 92 and front housing 20 may be used to achieve this effect.

In any embodiment, it is preferable to define the maximum exposed length of the needle 76 (i.e. the axial extension of the needle 76 beyond the front housing 20, or any other structure attached forwardly of the front housing 20, e.g. the retractable needle sleeve 90 in its retracted position) so as to correspond to a desired depth of medicament delivery. In some circumstances, it may be desirable for the needle 76 to penetrate the delivery site at 90° to the surface of the delivery site such that the exposed length of the needle 76 is equal to the depth of medicament delivery below the surface of the delivery site (e.g. a surface of skin). In other circumstances, it may be desirable for the needle 76 to penetrate the delivery site at an angle other than 90° relative to the delivery site. In such cases, the exposed length of needle 76 should be longer so as to achieve the desired depth of medicament delivery below the surface of the delivery site when fully inserted to its maximal extent. The device 10,10' may include an interface at a front end providing the user with a visual cue with regards to the intended angle of delivery. For example, a forward surface of the front housing 20 may be inclined at 45° relative to the longitudinal axis so determine the maximal delivery depth and provide a visual cue to the user to insert the needle 76 into the delivery site at 45° relative to the surface of the delivery site. Alternatively, the sub-assembly may include a series of points that are each the axially most forward point of the sub-assembly at a given radii, and wherein the series of points lie in a plane that is inclined relative to a longitudinal axis of the sub-assembly, wherein the angle of inclination of the plane determines a minimum angle at which the needle may be inserted into a delivery site.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The readers attention is directed to all papers and documents which are filed concurrently with or previous to this specification in connection with this application and which are open to public inspection with this specification, and the contents of all such papers and documents are incorporated herein by reference.

The invention claimed is:

1. A sub-assembly for a medicament delivery device, the sub-assembly comprising:
   a housing;
   a propellant source contained in and axially moveable relative to said housing; and
   a button axially moveable relative to said housing, at least a part of said button being disposed axially rearwardly of a part of said propellant source;
   wherein the button includes one or more radially flexible blocking members, and the button is moveable between a first axial position in which the one or more radially flexible blocking members are radially restrained by the housing in a radially inward position that limits rearward axial movement of the propellant source, and a second axial position in which the one or more radially flexible blocking members are movable from the radially inward position to a radially outward position by a rearwardly axial force acting on the one or more radially flexible blocking members and permit rearward axial movement of the propellant source relative to the button and the housing;
   wherein the rearwardly axial force is created by a vapor pressure following release of a propellant from the propellant source.

2. The sub-assembly according to claim 1, wherein the one or more radially flexible blocking members have a tapered front surface such that the one or more radially flexible blocking members are moveable from the radially inward position to the radially outward position by the rearwardly axial force acting on the tapered front surface when in the second axial position.

3. The sub-assembly according to claim 1, wherein the housing includes a rear housing and a front housing, and axially rearward movement of the propellant source relative to the housing causes a retraction biasing member to delatch, wherein the delatched retraction biasing member urges the rear housing axially rearwardly relative to the front housing.

4. The sub-assembly according to claim 3, wherein the retraction biasing member is delatched when latch heads are moved from a radially inward position to a radially outward position.

5. The sub-assembly according to claim 4, wherein the axially rearward movement of the propellant source relative to the housing permits axially rearward movement of a plug, wherein axially rearward movement of the plug urges the latch heads from the radially inward position to the radially outward position.

6. The sub-assembly according to claim 5, wherein the latch heads are disposed on radially flexible legs, and wherein the plug includes hooks that are engageable with the radially flexible legs so as to prevent the radially flexible legs from flexing radially outwardly, the hooks being capable of disengaging the radially flexible legs when the plug moves axially rearwardly relative to the radially flexible legs.

7. The sub-assembly according to claim 4, wherein the latch heads are formed on an inner housing and the latch heads are axially aligned with first stops of the front housing when in the radially outward position, and wherein abutment between the latch heads and first stops prevents axially rearward movement of the inner housing relative to the front housing.

8. The sub-assembly according to claim 3, wherein one of the front housing and rear housing includes second stops and the other of the front housing and rear housing includes lock out elements, wherein engagement between the second stops and lock out elements prevents forwardly and rearwardly axial movement of the rear housing relative to the front housing, and wherein the second stops are engageable in the lock out elements when the rear housing is axially rearwardly displaced relative to the front housing by a predetermined axial distance.

9. The sub-assembly according to claim 1, further comprising one or more latches on one of the button or the housing, wherein the one or more latches engage the other of the button or the housing when the button is in the second axial position, and wherein engagement of the one or more latches prevents axially rearward movement of the button relative to the housing.

10. The sub-assembly according to claim 1, further comprising a needle sleeve wherein the needle sleeve is axially moveable relative to the housing between a forward axial position and a rearward axial position, wherein in the rearward axial position the needle sleeve determines maximum axial length of a needle extending therethrough relative to the needle sleeve.

11. The sub-assembly according to claim 10, further including a biasing member that biases the needle sleeve towards the forward axial position relative to the housing.

12. The sub-assembly according to claim 1, wherein a forward surface of the sub-assembly is inclined relative to a longitudinal axis of the sub-assembly, wherein an angle of inclination of the forward surface determines an angle at which the sub-assembly may be held against a delivery site to achieve maximum penetration of a needle extending from the sub-assembly.

13. The sub-assembly according to claim 1, wherein the sub-assembly includes a series of points that are each an axially most forward point of the sub-assembly at a given radii, and wherein the series of points lie in a plane that is inclined relative to a longitudinal axis of the sub-assembly, wherein an angle of inclination of the plane determines a minimum angle at which a needle of a syringe mounted in the sub-assembly may be inserted into a delivery site.

14. The sub-assembly according to claim 1, were the propellant source comprises a reservoir housing defining a reservoir for containing the propellant, and a stem having a bore therethrough, at least one inlet in fluid communication with the bore, and an open outlet end in fluid communication with the bore, the stem being moveable relative to the reservoir housing between a first position in which the at least one inlet is not in fluid communication with the reservoir and a second position in which the at least one inlet is in fluid communication with the bore.

15. The sub-assembly according to claim 14, wherein the propellant source further comprising a biasing member for biasing the stem towards the first position.

16. The sub-assembly according to claim 14, wherein the reservoir contains a liquefied gas propellant.

17. The sub-assembly according to claim 14, wherein the reservoir contains the propellant that is or contains a hydrofluoroalkane (HFA).

18. The sub-assembly according to claim 17, wherein the propellant is or contains HFA134a.

19. A medicament delivery device comprising:
a sub-assembly comprising:
a housing;
a propellant source contained in and axially moveable relative to said housing; and
a button axially moveable relative to said housing, at least a part of said button being disposed axially rearwardly of a part of said propellant source;
wherein the button includes one or more radially flexible blocking members, and the button is moveable between a first axial position in which the one or more radially flexible blocking members are radially restrained by the housing in a radially inward position that limits rearward axial movement of the propellant source, and a second axial position in which the one or more radially flexible blocking members are movable from the radially inward position to a radially outward position by a rearwardly axial force acting on the one or more radially flexible blocking members and permit rearward axial movement of the propellant source relative to the button and the housing;
wherein the rearwardly axial force is created by a vapor pressure following release of a propellant from the propellant source; and
a syringe connected to the sub-assembly, wherein the syringe includes a barrel for containing a medicament, the barrel having an outlet at a front end, and a stopper axially moveable in the barrel.

20. The medicament delivery device according to claim 19 wherein the syringe further includes a needle in fluid communication with the outlet.

21. The medicament delivery device according to claim 19, wherein:
the housing includes a rear housing and a front housing, and axially rearward movement of the propellant source relative to the housing causes a retraction biasing member to delatch, wherein the delatched retraction biasing member urges the rear housing axially rearwardly relative to the front housing; and
the syringe is axially restrained relative to the rear housing such that axial movement of the rear housing relative to the front housing causes axial movement of the syringe relative to the front housing.

22. A sub-assembly for a medicament delivery device, the sub-assembly comprising:
a housing;
a propellant source contained in and axially moveable relative to said housing; and
a button axially moveable relative to said housing, at least a part of said button being disposed axially rearwardly of a part of said propellant source;
wherein the button includes one or more radially flexible blocking members, and the button is moveable between a first axial position in which the one or more radially flexible blocking members are radially restrained by the housing in a radially inward position that limits rearward axial movement of the propellant source, and a second axial position in which the one or more radially flexible blocking members are able to flex to a radially outward position and permit rearward axial movement of the propellant source relative to the button and the housing;
wherein the housing includes a rear housing and a front housing, and axially rearward movement of the propellant source relative to the housing causes a retraction biasing member to delatch, wherein the delatched retraction biasing member urges the rear housing axially rearwardly relative to the front housing;
wherein the retraction biasing member is delatched when latch heads are moved from a radially inward position to a radially outward position.

* * * * *